United States Patent
Brunnett et al.

(10) Patent No.: US 10,543,089 B2
(45) Date of Patent: *Jan. 28, 2020

(54) ANNULOPLASTY RING WITH REDUCED DEHISCENCE

(71) Applicant: Edwards Lifesciences Corporation, Irvine, CA (US)

(72) Inventors: William C. Brunnett, Mission Viejo, CA (US); Alison S. Curtis, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 216 days.

This patent is subject to a terminal disclaimer.

(21) Appl. No.: 15/333,055

(22) Filed: Oct. 24, 2016

(65) Prior Publication Data

US 2017/0042679 A1    Feb. 16, 2017

Related U.S. Application Data

(60) Continuation of application No. 14/595,075, filed on Jan. 12, 2015, now Pat. No. 9,474,607, which is a
(Continued)

(51) Int. Cl.
*A61F 2/24* (2006.01)
(52) U.S. Cl.
CPC .......... *A61F 2/2445* (2013.01); *A61F 2/2442* (2013.01); *A61F 2/2448* (2013.01);
(Continued)
(58) Field of Classification Search
CPC .................................................... A61F 2/2445
See application file for complete search history.

(56) References Cited

U.S. PATENT DOCUMENTS

| 3,656,185 A | 4/1972 | Carpentier |
| 4,055,861 A | 11/1977 | Carpentier et al. |

(Continued)

FOREIGN PATENT DOCUMENTS

| EP | 0338994 A1 | 10/1989 |
| EP | 0860151 A1 | 8/1998 |

(Continued)

OTHER PUBLICATIONS

Adams, David, et al., "Large Annuloplasty Rings Facilitate Mitral Valve Repair in Barlow's Disease," Society of Thoracic Surgeons 42nd Annual Meeting, Jan. 30-Feb. 1, 2006.

(Continued)

*Primary Examiner* — Jacqueline Woznicki
(74) *Attorney, Agent, or Firm* — Guy Cumberbatch

(57) ABSTRACT

A prosthetic remodeling annuloplasty ring for use in tricuspid or mitral valve repairs to provide support after annuloplasty surgery. The annuloplasty ring includes a relatively rigid core extending around an axis that is discontinuous to define two free ends. A suture-permeable interface surrounding the core includes floppy regions adjacent both free ends of the core. Sutures are used to attach the annuloplasty ring to the annulus, including at least one suture through each of the floppy regions to secure the free ends of the ring and minimize the risk of ring dehiscence, or pull through of the sutures through the annulus tissue. The floppy regions may project from each free end into the gap toward each other, be radially enlarged such as paddle-like extensions, or may comprise outwardly lateral extensions at the free ends of the core.

20 Claims, 5 Drawing Sheets

Related U.S. Application Data division of application No. 13/305,546, filed on Nov. 28, 2011, now Pat. No. 8,932,350.

(60) Provisional application No. 61/418,190, filed on Nov. 30, 2010.

(52) U.S. Cl.
CPC ............... *A61F 2210/0076* (2013.01); *A61F 2220/0008* (2013.01); *A61F 2230/0004* (2013.01); *A61F 2230/0008* (2013.01); *A61F 2230/0013* (2013.01); *A61F 2250/0019* (2013.01); *A61F 2250/0036* (2013.01)

(56) References Cited

U.S. PATENT DOCUMENTS

| | | | |
|---|---|---|---|
| 4,164,046 | A | 8/1979 | Cooley |
| 4,217,665 | A | 8/1980 | Bex et al. |
| 4,275,469 | A | 6/1981 | Gabbay |
| 4,602,911 | A | 7/1986 | Ahmadi et al. |
| 4,790,844 | A | 12/1988 | Ovil |
| 4,917,097 | A | 4/1990 | Proudian et al. |
| 4,993,428 | A | 2/1991 | Arms |
| 5,010,892 | A | 4/1991 | Colvin et al. |
| 5,041,130 | A | 8/1991 | Cosgrove et al. |
| 5,061,277 | A * | 10/1991 | Carpentier ............ A61F 2/2448 623/2.36 |
| 5,064,431 | A | 11/1991 | Gilbertson et al. |
| 5,104,407 | A | 4/1992 | Lam et al. |
| 5,201,880 | A | 4/1993 | Wright et al. |
| 5,258,021 | A | 11/1993 | Duran |
| 5,306,296 | A | 4/1994 | Wright et al. |
| 5,316,016 | A | 5/1994 | Adams et al. |
| 5,344,442 | A | 9/1994 | Deac |
| 5,396,887 | A | 3/1995 | Imran |
| 5,397,348 | A | 3/1995 | Campbell et al. |
| 5,450,860 | A | 9/1995 | O'Connor |
| 5,480,424 | A | 1/1996 | Cox |
| 5,496,336 | A | 3/1996 | Cosgrove et al. |
| 5,533,515 | A | 7/1996 | Caller et al. |
| 5,573,007 | A | 11/1996 | Bobo, Sr. |
| 5,593,435 | A | 1/1997 | Carpentier et al. |
| 5,607,471 | A | 3/1997 | Seguin et al. |
| 5,662,704 | A | 9/1997 | Gross |
| 5,674,279 | A | 10/1997 | Wright et al. |
| 5,716,397 | A | 2/1998 | Myers |
| 5,728,064 | A | 3/1998 | Burns et al. |
| 5,733,331 | A | 3/1998 | Peredo |
| 5,752,522 | A | 5/1998 | Murphy |
| 5,776,189 | A | 7/1998 | Khalid |
| 5,814,098 | A | 9/1998 | Hinnenkamp et al. |
| 5,824,066 | A | 10/1998 | Gross |
| 5,824,069 | A | 10/1998 | Lemole |
| 5,848,969 | A | 12/1998 | Panescu et al. |
| 5,855,563 | A | 1/1999 | Kaplan et al. |
| 5,865,801 | A | 2/1999 | Houser |
| 5,888,240 | A | 3/1999 | Carpentier et al. |
| 5,902,308 | A | 5/1999 | Murphy |
| 5,919,147 | A | 7/1999 | Jain |
| 5,921,934 | A | 7/1999 | Teo |
| 5,921,935 | A | 7/1999 | Hickey |
| 5,924,984 | A | 7/1999 | Rao |
| 5,931,868 | A | 8/1999 | Gross |
| 5,957,977 | A | 9/1999 | Melvin |
| 5,972,030 | A | 10/1999 | Garrison et al. |
| 6,010,531 | A | 1/2000 | Donlon et al. |
| 6,019,739 | A | 2/2000 | Rhee et al. |
| 6,024,918 | A | 2/2000 | Hendriks et al. |
| 6,042,554 | A | 3/2000 | Rosenman et al. |
| 6,066,160 | A | 5/2000 | Colvin et al. |
| 6,074,417 | A | 6/2000 | Peredo |
| 6,081,737 | A | 6/2000 | Shah |
| 6,083,179 | A | 7/2000 | Oredsson |
| 6,099,475 | A | 8/2000 | Seward et al. |
| 6,102,945 | A | 8/2000 | Campbell |
| 6,110,200 | A | 8/2000 | Hinnenkamp |
| 6,117,091 | A | 9/2000 | Young et al. |
| 6,143,024 | A | 11/2000 | Campbell et al. |
| 6,159,240 | A | 12/2000 | Sparer et al. |
| 6,183,512 | B1 | 2/2001 | Howanec, Jr. et al. |
| 6,187,040 | B1 | 2/2001 | Wright |
| 6,217,610 | B1 * | 4/2001 | Carpentier ............ A61F 2/2448 623/2.37 |
| 6,231,602 | B1 | 5/2001 | Carpentier et al. |
| 6,250,308 | B1 | 6/2001 | Cox |
| 6,258,122 | B1 | 7/2001 | Tweden et al. |
| 6,312,464 | B1 | 11/2001 | Navia |
| 6,332,893 | B1 | 12/2001 | Mortier et al. |
| 6,368,348 | B1 | 4/2002 | Gabbay |
| 6,391,054 | B2 | 5/2002 | Carpentier et al. |
| 6,406,420 | B1 | 6/2002 | McCarthy et al. |
| 6,406,493 | B1 | 6/2002 | Tu et al. |
| 6,409,759 | B1 | 6/2002 | Peredo |
| 6,416,548 | B2 | 7/2002 | Chinn et al. |
| 6,419,696 | B1 | 7/2002 | Ortiz et al. |
| 6,602,288 | B1 | 8/2003 | Cosgrove et al. |
| 6,602,289 | B1 * | 8/2003 | Colvin ................. A61F 2/2448 623/2.37 |
| 6,619,291 | B2 | 9/2003 | Hlavka et al. |
| 6,629,534 | B1 | 10/2003 | St. Goar et al. |
| 6,689,164 | B1 | 2/2004 | Seguin |
| 6,709,456 | B2 | 3/2004 | Langberg et al. |
| 6,718,985 | B2 | 4/2004 | Hlavka et al. |
| 6,719,786 | B2 | 4/2004 | Ryan et al. |
| 6,723,038 | B1 | 4/2004 | Schroeder et al. |
| 6,726,715 | B2 | 4/2004 | Sutherland |
| 6,726,717 | B2 | 4/2004 | Alfieri et al. |
| 6,730,121 | B2 | 5/2004 | Ortiz et al. |
| 6,749,630 | B2 | 6/2004 | McCarthy et al. |
| 6,749,639 | B2 | 6/2004 | Lewallen |
| 6,764,510 | B2 | 7/2004 | Vidlund et al. |
| 6,797,002 | B2 | 9/2004 | Spence et al. |
| 6,800,090 | B2 | 10/2004 | Alferness et al. |
| 6,802,860 | B2 | 10/2004 | Cosgrove et al. |
| 6,805,710 | B2 | 10/2004 | Bolling et al. |
| 6,805,711 | B2 | 10/2004 | Quijano et al. |
| 6,830,586 | B2 | 12/2004 | Quijano et al. |
| 6,858,039 | B2 | 2/2005 | McCarthy |
| 6,908,482 | B2 | 6/2005 | McCarthy et al. |
| 6,918,917 | B1 | 7/2005 | Nguyen et al. |
| 6,921,407 | B2 | 7/2005 | Nguyen et al. |
| 6,942,694 | B2 | 9/2005 | Liddicoat et al. |
| 6,945,996 | B2 | 9/2005 | Sedransk |
| 6,955,689 | B2 | 10/2005 | Ryan et al. |
| 6,966,924 | B2 | 11/2005 | Holmberg |
| 6,977,950 | B1 | 12/2005 | Krishnamoorthy |
| 6,986,775 | B2 | 1/2006 | Morales et al. |
| 6,997,950 | B2 | 2/2006 | Chawla |
| 7,037,334 | B1 | 5/2006 | Hlavka et al. |
| 7,066,954 | B2 | 6/2006 | Ryan et al. |
| 7,087,079 | B2 | 8/2006 | Navia et al. |
| 7,101,395 | B2 | 9/2006 | Tremulis et al. |
| 7,112,219 | B2 | 9/2006 | Vidlund et al. |
| 7,118,595 | B2 | 10/2006 | Ryan et al. |
| 7,125,421 | B2 | 10/2006 | Tremulis et al. |
| 7,166,126 | B2 | 1/2007 | Spence et al. |
| 7,166,127 | B2 | 1/2007 | Spence et al. |
| 7,189,258 | B2 | 3/2007 | Johnson et al. |
| 7,247,134 | B2 | 7/2007 | Vidlund et al. |
| 7,294,148 | B2 | 11/2007 | McCarthy |
| 7,329,280 | B2 | 2/2008 | Bolling et al. |
| 7,361,190 | B2 | 4/2008 | Shaoulian et al. |
| 7,367,991 | B2 | 5/2008 | McCarthy et al. |
| 7,371,259 | B2 | 5/2008 | Ryan et al. |
| 7,377,940 | B2 | 5/2008 | Ryan et al. |
| 7,452,376 | B2 | 11/2008 | Lim et al. |
| 7,527,647 | B2 | 5/2009 | Spence |
| 7,608,103 | B2 | 10/2009 | McCarthy |
| 7,642,684 | B2 | 1/2010 | Himmelmann et al. |
| 7,879,087 | B2 | 2/2011 | Roberts |
| 7,927,370 | B2 | 4/2011 | Webler et al. |
| 7,942,928 | B2 | 5/2011 | Webler et al. |
| 7,959,673 | B2 | 6/2011 | Carpentier et al. |

(56) References Cited

U.S. PATENT DOCUMENTS

| | | |
|---|---|---|
| 7,993,395 B2 | 8/2011 | Vanermen et al. |
| 8,123,802 B2 | 2/2012 | Kron et al. |
| 8,460,173 B2 | 6/2013 | Schweich, Jr. et al. |
| 8,535,374 B2 | 9/2013 | Redmond et al. |
| 8,591,576 B2 | 11/2013 | Hasenkam et al. |
| 8,734,507 B2 | 5/2014 | Keranen |
| 8,764,821 B2 | 7/2014 | Carpentier et al. |
| 2001/0010018 A1 | 7/2001 | Cosgrove et al. |
| 2001/0021874 A1 | 9/2001 | Carpentier et al. |
| 2001/0034551 A1 | 10/2001 | Cox |
| 2001/0049557 A1 | 12/2001 | Chinn et al. |
| 2002/0129820 A1* | 9/2002 | Ryan ............... A61F 2/2445 128/858 |
| 2002/0133180 A1 | 9/2002 | Ryan et al. |
| 2002/0169504 A1 | 11/2002 | Alferness et al. |
| 2002/0173844 A1 | 11/2002 | Alfieri et al. |
| 2003/0033009 A1 | 2/2003 | Gabbay |
| 2003/0040793 A1 | 2/2003 | Marquez |
| 2003/0045929 A1 | 3/2003 | McCarthy et al. |
| 2003/0050693 A1 | 3/2003 | Quijano et al. |
| 2003/0078653 A1 | 4/2003 | Vesely et al. |
| 2003/0083742 A1 | 5/2003 | Spence et al. |
| 2003/0093148 A1 | 5/2003 | Bolling et al. |
| 2003/0105519 A1 | 6/2003 | Fasol et al. |
| 2003/0176917 A1 | 9/2003 | Ryan et al. |
| 2003/0199975 A1 | 10/2003 | Gabbay |
| 2003/0208264 A1* | 11/2003 | McCarthy ........... A61F 2/2445 623/2.11 |
| 2004/0006384 A1 | 1/2004 | McCarthy |
| 2004/0088047 A1 | 5/2004 | Spence et al. |
| 2004/0122513 A1 | 6/2004 | Navia et al. |
| 2004/0186566 A1 | 9/2004 | Hindrichs et al. |
| 2004/0249452 A1 | 12/2004 | Adams et al. |
| 2004/0249453 A1 | 12/2004 | Cartledge et al. |
| 2005/0004665 A1 | 1/2005 | Aklog |
| 2005/0004666 A1 | 1/2005 | Alfieri et al. |
| 2005/0004669 A1 | 1/2005 | Sievers |
| 2005/0038509 A1 | 2/2005 | Ashe |
| 2005/0043791 A1 | 2/2005 | McCarthy et al. |
| 2005/0070999 A1 | 3/2005 | Spence |
| 2005/0075727 A1 | 4/2005 | Wheatley |
| 2005/0131533 A1* | 6/2005 | Alfieri ............... A61F 2/2448 623/2.36 |
| 2005/0182487 A1 | 8/2005 | McCarthy et al. |
| 2005/0192666 A1 | 9/2005 | McCarthy |
| 2005/0197696 A1 | 9/2005 | Gomez Duran |
| 2005/0246014 A1 | 11/2005 | McCarthy |
| 2005/0256567 A1 | 11/2005 | Lim et al. |
| 2005/0256568 A1 | 11/2005 | Lim et al. |
| 2005/0256569 A1 | 11/2005 | Lim et al. |
| 2005/0267572 A1 | 12/2005 | Schoon et al. |
| 2005/0278022 A1 | 12/2005 | Lim |
| 2005/0288776 A1 | 12/2005 | Shaoulian et al. |
| 2005/0288777 A1 | 12/2005 | Rhee et al. |
| 2005/0288778 A1 | 12/2005 | Shaoulian et al. |
| 2005/0288780 A1 | 12/2005 | Rhee et al. |
| 2005/0288781 A1 | 12/2005 | Moaddeb et al. |
| 2005/0288782 A1 | 12/2005 | Moaddeb et al. |
| 2005/0288783 A1 | 12/2005 | Shaoulian et al. |
| 2006/0015178 A1 | 1/2006 | Moaddeb et al. |
| 2006/0015179 A1 | 1/2006 | Bulman-Fleming et al. |
| 2006/0020336 A1 | 1/2006 | Liddicoat |
| 2006/0025856 A1 | 2/2006 | Ryan et al. |
| 2006/0025858 A1 | 2/2006 | Alameddine |
| 2006/0030885 A1 | 2/2006 | Hyde |
| 2006/0129236 A1 | 6/2006 | McCarthy |
| 2006/0149368 A1 | 7/2006 | Spence |
| 2006/0184241 A1 | 8/2006 | Marquez |
| 2006/0195183 A1 | 8/2006 | Navia et al. |
| 2006/0206203 A1 | 9/2006 | Yang et al. |
| 2006/0229708 A1 | 10/2006 | Powell et al. |
| 2006/0259135 A1 | 11/2006 | Navia et al. |
| 2006/0282162 A1* | 12/2006 | Nguyen ............. A61F 2/2445 623/2.11 |
| 2007/0038294 A1 | 2/2007 | Navia |
| 2007/0038296 A1 | 2/2007 | Navia et al. |
| 2007/0049952 A1 | 3/2007 | Weiss |
| 2007/0050020 A1 | 3/2007 | Spence |
| 2007/0066863 A1 | 3/2007 | Rafiee et al. |
| 2007/0100439 A1 | 5/2007 | Cangialosi et al. |
| 2007/0100441 A1 | 5/2007 | Kron et al. |
| 2007/0118151 A1 | 5/2007 | Davidson |
| 2007/0123979 A1 | 5/2007 | Perier et al. |
| 2007/0156234 A1 | 7/2007 | Adzich et al. |
| 2007/0162111 A1 | 7/2007 | Fukamachi et al. |
| 2007/0162112 A1 | 7/2007 | Burriesci et al. |
| 2007/0173930 A1 | 7/2007 | Sogard et al. |
| 2007/0173931 A1 | 7/2007 | Tremulis et al. |
| 2007/0191940 A1 | 8/2007 | Arru et al. |
| 2007/0213582 A1 | 9/2007 | Zollinger et al. |
| 2007/0255036 A1 | 11/2007 | Douk et al. |
| 2007/0299513 A1 | 12/2007 | Ryan et al. |
| 2008/0058924 A1 | 3/2008 | Ingle et al. |
| 2008/0086203 A1 | 4/2008 | Roberts |
| 2008/0091059 A1 | 4/2008 | Machold et al. |
| 2009/0036979 A1 | 2/2009 | Redmond et al. |
| 2009/0043381 A1 | 2/2009 | Macoviak et al. |
| 2009/0132036 A1 | 5/2009 | Navia |
| 2009/0157176 A1 | 6/2009 | Carpentier et al. |
| 2009/0177276 A1 | 7/2009 | Carpentier et al. |
| 2009/0177278 A1 | 7/2009 | Spence |
| 2009/0192602 A1 | 7/2009 | Kuehn |
| 2009/0192603 A1 | 7/2009 | Ryan |
| 2009/0192604 A1 | 7/2009 | Gloss |
| 2009/0192605 A1 | 7/2009 | Gloss et al. |
| 2009/0192606 A1 | 7/2009 | Gloss et al. |
| 2009/0264996 A1 | 10/2009 | Vanermen et al. |
| 2009/0276038 A1 | 11/2009 | Tremulis et al. |
| 2009/0287303 A1 | 11/2009 | Carpentier |
| 2010/0076549 A1 | 3/2010 | Keidar et al. |
| 2010/0076551 A1 | 3/2010 | Drake |
| 2010/0145440 A1 | 6/2010 | Keranen |
| 2010/0152844 A1 | 6/2010 | Couetil |
| 2010/0168845 A1 | 7/2010 | Wright |
| 2010/0174365 A1 | 7/2010 | Parravicini et al. |
| 2010/0280604 A1* | 11/2010 | Zipory ............. A61B 17/0401 623/2.11 |
| 2010/0286767 A1* | 11/2010 | Zipory ............. A61F 2/2445 623/2.11 |
| 2013/0204361 A1 | 8/2013 | Adams et al. |

FOREIGN PATENT DOCUMENTS

| | | |
|---|---|---|
| EP | 1034753 A1 | 9/2000 |
| WO | 9742871 A1 | 11/1997 |
| WO | 0147438 A1 | 7/2001 |
| WO | 03034950 A1 | 5/2003 |
| WO | 2005004753 A1 | 1/2005 |
| WO | 05034813 A2 | 4/2005 |
| WO | 2008063537 A2 | 5/2008 |

OTHER PUBLICATIONS

Alonso-Lei, M.D., et al., Adjustable Annuloplasty for Tricuspid Insufficiency, The annals of Thoracic Surgery, vol. 46, No. 3, pp. 368-369, Sep. 1988.

Bolling, et al., Surgical Alternatives for Heart Failure, The Journal of Heart and Lung Transplantation, vol. 20, No. 7, pp. 729-733, 2001.

Bolling, Mitral Valve Reconstruction in the Patient With Heart Failure, Heart Failure Reviews, 6, pp. 177-185, 2001.

Carpentier, et al. "The 'Physio-Ring': An Advanced Concept in Mitral Valve Annuloplasty," Society of Thoracic Surgeons 31st Annual meeting, Jan. 30-Feb. 2, 1995.

Carpentier, et al., Reconstructive Valve Surgery, Chapter 19—Reconstructive Techniques, ISBN No. 978-0-7216-9168-8, Sanders Elsevier Publishing, Maryland Heights, Missouri, 2010.

Carpentier-Edwards Classic Annuloplasty Ring With Duraflo Treatment Models 4425 and 4525 for Mitral and Tricuspid Valvuloplsty, Baxter Healthcare Corporation, 1998.

Carpentier-Edwards Pyshio Annuloplasty Ring, Edwards Lifesciences Corporation, 2003.

(56) References Cited

OTHER PUBLICATIONS

Cochran, et al., Effect of Papillary Muscle Position on Mitral Valve Function: Relationship to Homografts, The Society of Thoracic Surgeons, pp. 5155-5161,1998.
D.C. Miller, IMR Redux—to Repair or Replace?, Journal of Thoracic & Cardiovascular Surgery, pp. 1-8,2001.
Edwards Lifesciences MC3Tricuspid Annuloplasty System brochure. Copyright 2006.
Flachskampf, Frank A., et al. "Analysis of Shape and Motion of the Mitral Annulus in Subjects With and Without Cardiomyopathy by Echocardiographic 3-Dimensional Reconstruction," American Society of Echocardiography 0894-7317/2000.
Gatti, et al., Preliminary Experience in Mitral Valve Repair Using the Cosgrove-Edwards Annuloplasty Ring, Interactive Cardiovascular and Thoracic Surgery, vol. 2(3), pp. 256-261, 2003.
Melo, et al., Atrioventricular Valve Repair Using Externally Adjustable Flexible Rings: The Journal of Thoracic Cardiovascular Surgery, vol. 110, No. 5, 1995.
MGH Study Shows Mitral Valve Prolapse Not a Stroke Risk Factor, Massachusetts General Hospital, pp. 1-3, Jun. 1999.
Miller, D. Craig, M.D., "Ischemic Mitral Regurgitation Redux—to Repair or Replace?", The Journal of Thoracic & Cardiovascular Surgery, Dec. 2001, vol. 122, No. 6, pp. 1059-1062.
Salgo, et al., Effect of Annular Shape on Leaflet Curvature in Reducing Mitral Leaflet, American Heart Association, Circulation 2002; pp. 106-711.
Seguin, et al., Advance in Mitral Valve Repair Using a Device Flexible in Three Dimensions, The St. Jude Medical-Seguin Annuloplasty Ring, ASAIO Journal, vol. 42, No. 6, pp. 368-371, 1996.
Smolens, et al., Mitral Valve Repair in Heart Failure, The European Journal of Heart Failure 2, pp. 365-371, 2000.
Techniques for 3D Quantitative Echocardiography, University of Washington Cardiovascular Research & Training Center Cardiac Imaging Research Lab, pp. 1-5, Oct. 2003.
Watanabe, Nozomi, et al. "Mitral Annulus Flattens in Ischemic Mitral Regurgitation: Geometric Differences Between Inferior and Anterior Myocardial Infarction: A Real-Time 3-Dimensional Echocardiographic Study," American Heart Association © 2005; ISSN: 1524-4539.

\* cited by examiner

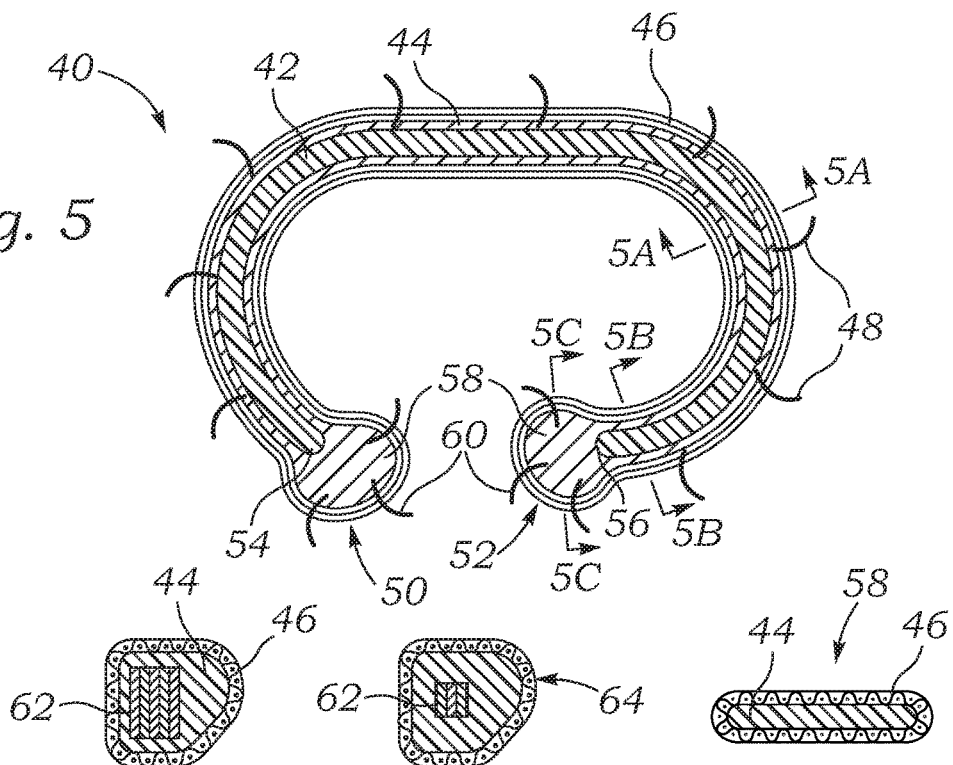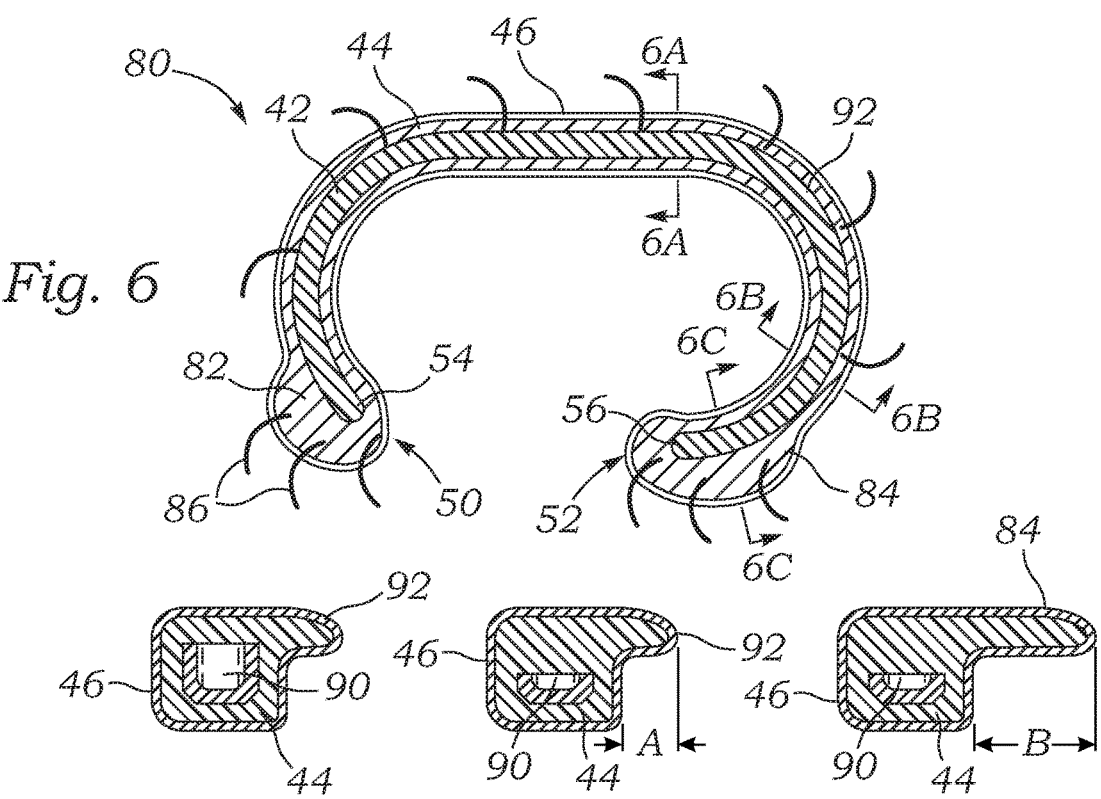

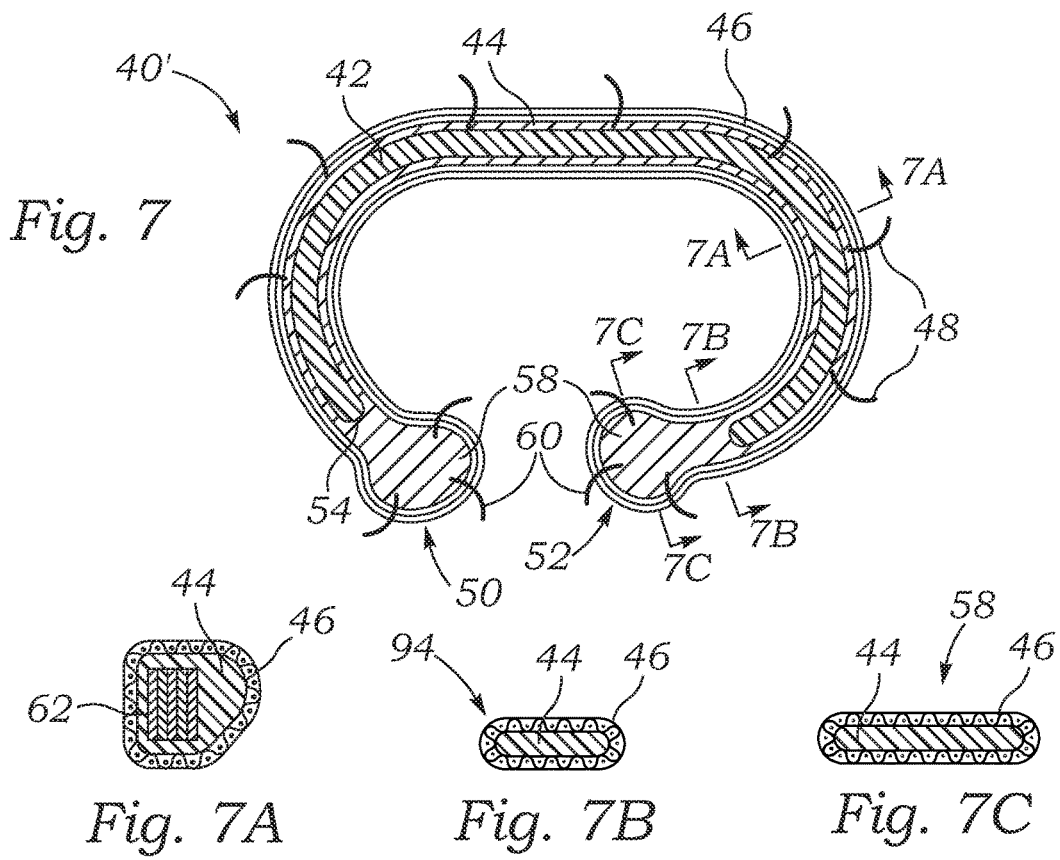
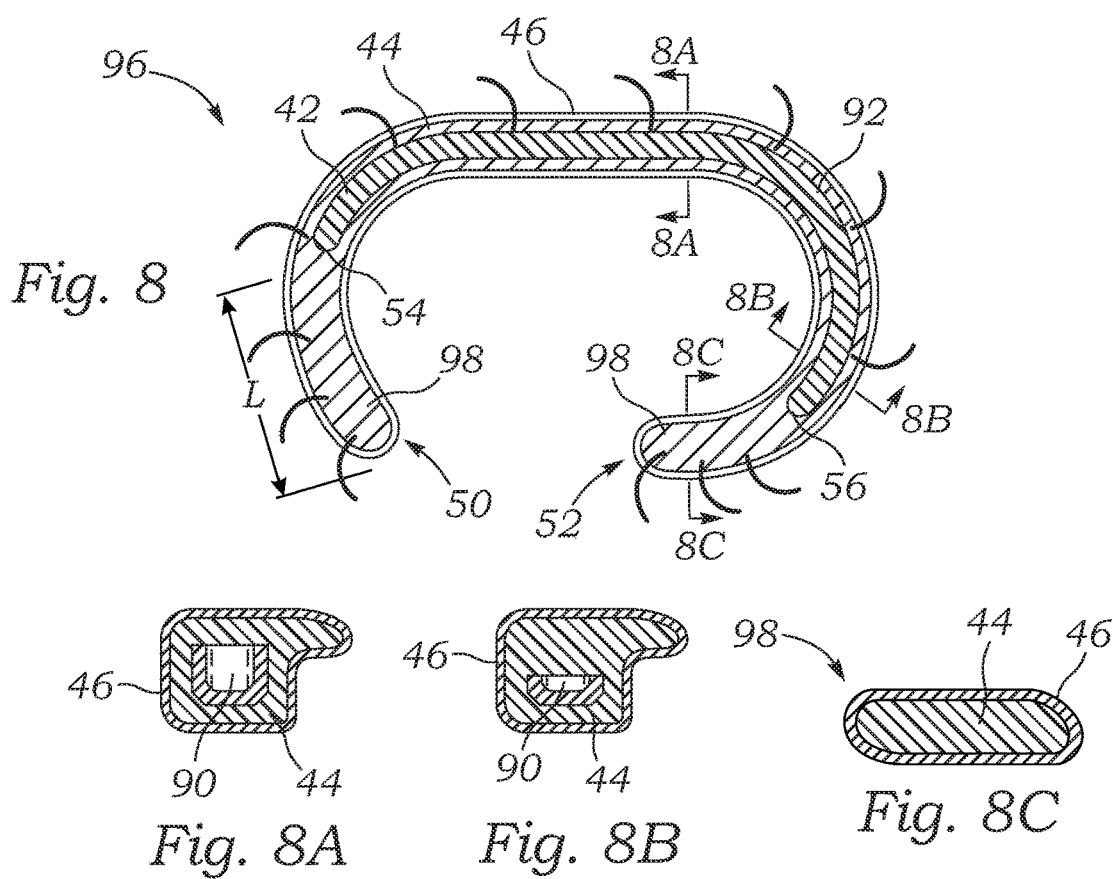

ANNULOPLASTY RING WITH REDUCED DEHISCENCE

CROSS REFERENCE TO RELATED APPLICATIONS

This application is a continuation of U.S. application Ser. No. 14/595,075, filed Jan. 12, 2015, now U.S. Pat. No. 9,474,607, which is a divisional of U.S. application Ser. No. 13/305,546, filed Nov. 28, 2011, now U.S. Pat. No. 8,932,350, which claims the benefit of U.S. Application No. 61/418,190, filed Nov. 30, 2010, the entire disclosures of which are incorporated by reference herein.

FIELD OF THE INVENTION

The present invention relates generally to methods of implanting medical devices in particular annuloplasty rings with reduced propensity for dehiscence.

BACKGROUND OF THE INVENTION

In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary, and are each mounted in an annulus comprising dense fibrous rings attached either directly or indirectly to the atrial and ventricular muscle fibers. Each annulus defines a flow orifice.

Valve disease can be severely debilitating and even fatal if left untreated. Various surgical techniques may be used to repair a diseased or damaged valve. Repair or reconstruction, as opposed to valve replacement, is typically used on minimally calcified valves. One repair technique that has been shown to be effective in treating incompetence is annuloplasty, in which the deformed valve annulus is reshaped by attaching a prosthetic annuloplasty repair segment or ring to the valve annulus. The annuloplasty ring is designed to support the functional changes that occur during the cardiac cycle: maintaining coaptation and valve integrity to prevent reverse flow while permitting good hemodynamics during forward flow.

The annuloplasty ring typically comprises an inner substrate of a metal such as rods or bands of stainless steel or titanium, or a flexible material such as silicone rubber or Dacron cordage, covered with a biocompatible fabric or cloth to allow the ring to be sutured to the fibrous annulus tissue. Annuloplasty rings may be stiff (e.g., titanium) or flexible (e.g., silicone), though a "remodeling" annuloplasty ring typically has an inner core that resists conforming to the native annulus shape and instead forces the annulus to conform to it. Rings may have a continuous periphery (e.g., D-shaped) or a discontinuous periphery with a gap between free ends (e.g., C-shaped). Examples are seen in U.S. Pat. Nos. 5,041,130, 5,104,407, 5,201,880, 5,258,021, 5,607,471 and 6,187,040. Most annuloplasty rings are formed in a plane, with some D-shaped mitral rings being bowed along their straight side to conform to the shape of the annulus at that location. Newer rings include a variety of three-dimensional shapes to correct particular anatomical pathologies; such as U.S. Pat. Nos. 6,805,710, 7,367,991, and 7,608,103.

Whether totally flexible, rigid, or semi-rigid, annuloplasty rings have been associated with a 10% to 15% ring dehiscence incidence at 10 years, thus requiring a reoperation. The present invention is intended to reduce this complication.

For the purposes of anatomic orientation, please refer to FIG. 1, which is a schematic representation of the atrioventricular (AV) junctions within the heart and the body in the left anterior oblique projection. The body is viewed in the upright position and has 3 orthogonal axes: superior-inferior, posterior-anterior, and right-left (lateral).

FIG. 2 is a cutaway view of the heart from the front, or anterior, perspective, with most of the primary structures marked. As is well known, the pathway of blood in the heart is from the right atrium to the right ventricle through the tricuspid valve, to and from the lungs, and from the left atrium to the left ventricle through the mitral valve. The present application has particular relevance to the repair of the tricuspid valve, which regulates blood flow between the right atrium and right ventricle, although certain aspects may apply to repair of other of the heart valves. The tricuspid and mitral valves together define the AV junctions.

As seen in FIG. 2, four structures embedded in the wall of the heart conduct impulses through the cardiac muscle to cause first the atria then the ventricles to contract. These structures are the sinoatrial node (SA node), the atrioventricular node (AV node), the bundle of His, and the Purkinje fibers. On the rear wall of the right atrium is a barely visible knot of tissue known as the sinoatrial, or SA node. This tiny area is the control of the heart's pacemaker mechanism. Impulse conduction normally starts in the SA node which generates a brief electrical impulse of low intensity approximately 72 times every minute in a resting adult. From this point the impulse spreads out over the sheets of tissue that make up the two atria, exciting the muscle fibers as it does so. This causes contraction of the two atria and thereby thrusts the blood into the empty ventricles. The impulse quickly reaches another small specialized knot of tissue known as the atrioventricular, or AV node, located between the atria and the ventricles. This node delays the impulse for about 0.07 seconds, which is exactly enough time to allow the atria to complete their contractions. When the impulses reach the AV node, they are relayed by way of the several bundles of His and Purkinje fibers to the ventricles, causing them to contract. As those of skill in the art are aware, the integrity and proper functioning of the conductive system of the heart is critical for good health.

FIG. 3 is a schematic view of the tricuspid valve orifice seen from its inflow side (from the right atrium), with the peripheral landmarks labeled as: antero septal commissure, anterior leaflet, antero posterior commissure, posterior leaflet, postero septal commissure, and septal leaflet. Contrary to traditional orientation nomenclature, the tricuspid valve is nearly vertical, as reflected by these sector markings.

From the same viewpoint, the tricuspid valve 20 is shown surgically exposed in FIG. 4 with an annulus 22 and three leaflets 24a, 24b, 24c extending inward into the flow orifice. Chordae tendineae 26 connect the leaflets to papillary muscles located in the right ventricle to control the movement of the leaflets. The tricuspid annulus 22 is an ovoid-shaped fibrous ring at the base of the valve that is less prominent than the mitral annulus, but larger in circumference.

Reflecting their true anatomic location, the three leaflets in FIG. 4 are identified as septal 24a, anterior 24b, and posterior (or "mural") 24c. The leaflets join together over three prominent zones of apposition, and the peripheral intersections of these zones are usually described as commissures 28. The leaflets 24 are tethered at the commissures 28 by the fan-shaped chordae tendineae 26 arising from prominent papillary muscles originating in the right ventricle. The septal leaflet 24a is the site of attachment to the fibrous trigone, the fibrous "skeletal" structure within the heart. The anterior leaflet 24*b*, largest of the 3 leaflets, often has notches. The posterior leaflet 24*c*, smallest of the 3 leaflets, usually is scalloped.

The ostium 30 of the right coronary sinus opens into the right atrium, and the tendon of Todaro 32 extends adjacent thereto. The AV node 34 and the beginning of the bundle of His 36 are located in the supero-septal region of the tricuspid valve circumference. The AV node 34 is situated directly on the right atrial side of the central fibrous body in the muscular portion of the AV septum, just superior and anterior to the ostium 30 of the coronary sinus 30. Measuring approximately 1.0 mm×3.0 mm×6.0 mm, the node is flat and generally oval shaped. The AV node 34 is located at the apex of the triangle of Koch 38, which is formed by the tricuspid annulus 22, the ostium 30 of the coronary sinus, and the tendon of Todaro 32. The AV node 34 continues on to the bundle of His 36, typically via a course inferior to the commissure 28 between the septal 24*a* and anterior 24*b* leaflets of the tricuspid valve; however, the precise course of the bundle of His 36 in the vicinity of the tricuspid valve may vary. Moreover, the location of the bundle of His 36 may not be readily apparent from a resected view of the right atrium because it lies beneath the annulus tissue.

The triangle of Koch 38 and tendon of Todaro 32 provide anatomic landmarks during tricuspid valve repair procedures. A major factor to consider during surgery is the proximity of the conduction system (AV node 34 and bundle of His 36) to the septal leaflet 24*a*. Of course, surgeons must avoid placing sutures too close to or within the AV node 34. C-shaped rings are good choices for tricuspid valve repairs because they allow surgeons to position the break in the ring adjacent the AV node 34, thus avoiding the need for suturing at that location.

One prior art rigid C-shaped ring of the prior art is the Carpentier-Edwards Classic® Tricuspid Annuloplasty Ring sold by Edwards Lifesciences Corporation of Irvine, Calif. Although not shown, the Classic® ring has an inner titanium core (not shown) covered by a layer of silicone and fabric. The Classic® ring is shaped and designed for downsizing diseased annuluses with Rheumatic Fever damage. The surgeon typically attaches the Classic® ring to the tricuspid annulus using single loop interrupted sutures along the outer edge of the ring.

Despite existing annuloplasty ring designs, there is a need for a prosthetic annuloplasty ring that has less propensity for dehiscence.

SUMMARY OF THE INVENTION

The present invention provides an annuloplasty ring including a relatively rigid inner core surrounded by a suture-impermeable interface. The core is discontinuous with two free ends separated across the gap, and the interface defines floppy regions adjacent each of the two free ends through which implant sutures are passed. Securing the floppy regions to the valve annulus helps position the annuloplasty ring while reducing ring dehiscence. The floppy regions may be enlarged radially or circumferentially, and may resemble paddle-like appendages or outwardly lateral wings.

A further understanding of the nature and advantages of the invention will become apparent by reference to the remaining portions of the specification and drawings.

BRIEF DESCRIPTION OF THE DRAWINGS

Features and advantages of the present invention will become appreciated as the same become better understood with reference to the specification, claims, and appended drawings wherein:

FIG. 5 is a longitudinal sectional view of an exemplary annuloplasty ring of the present application as seen from the atrial or inflow side of the ring;

FIGS. 5A-5C are lateral sectional views through several locations of the annuloplasty ring of FIG. 5 taken along respective sectional lines;

FIG. 6 is a longitudinal sectional view of an alternative annuloplasty ring of the present application as seen from the atrial or inflow side of the ring;

FIGS. 6A-6C are lateral sectional views through several locations of the annuloplasty ring of FIG. 6 taken along respective sectional lines;

FIG. 7 is a longitudinal sectional view of an alternative annuloplasty ring of the present application as seen from the atrial or inflow side of the ring;

FIGS. 7A-7C are lateral sectional views through several locations of the annuloplasty ring of FIG. 7 taken along respective sectional lines;

FIG. 8 is a longitudinal sectional view of another annuloplasty ring of the present application as seen from the atrial or inflow side of the ring;

FIGS. 8A-8C are lateral sectional views through several locations of the annuloplasty ring of FIG. 8 taken along respective sectional lines.

DETAILED DESCRIPTION OF THE PREFERRED EMBODIMENTS

Figure 1:
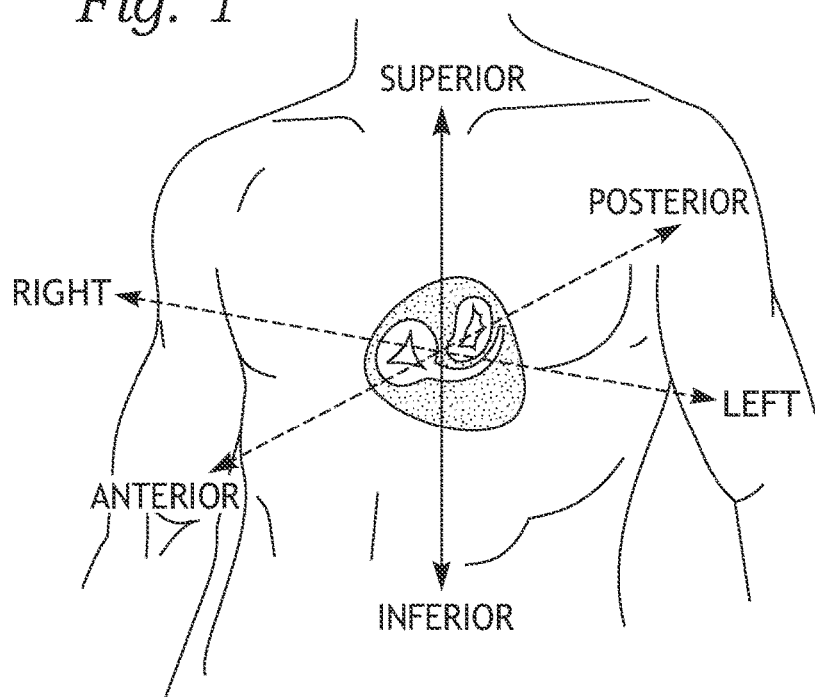
FIG. 1 is a schematic representation of the AV junctions within the heart and the body in the left anterior oblique projection.
Figure 2:
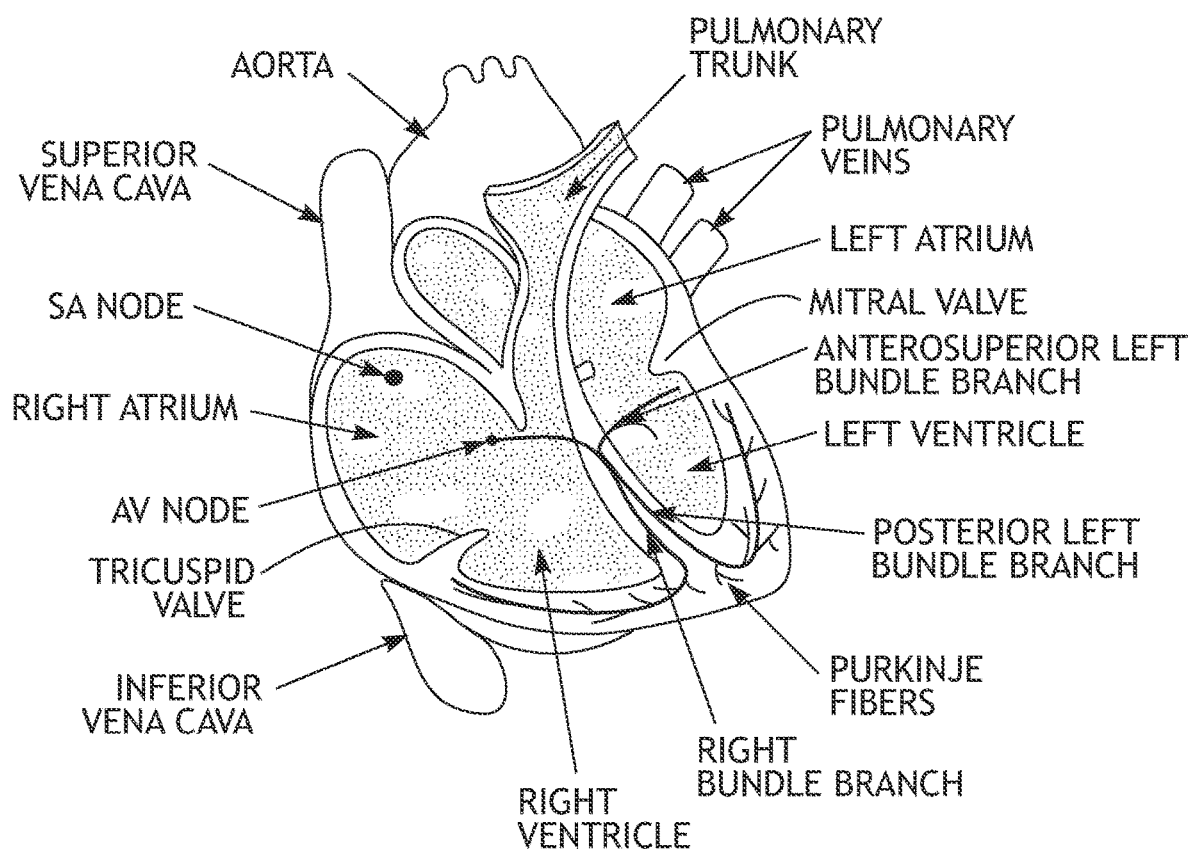
FIG. 2 is a cutaway view of the heart from the front, or anterior, perspective.

The present invention provides an improved tricuspid annuloplasty ring that better conforms to the native annulus and is configured to reduce dehiscence, or pull-through of sutures from annulus tissue, especially at the free ends of the ring.

It should also be understood that certain features of the present tricuspid ring might also be applicable and beneficial to rings for other of the heart's annuluses. For instance, the same structure might be used in a discontinuous ring for the mitral valve annulus.

The term "axis" in reference to the illustrated ring, and other non-circular or non-planar rings, refers to a line generally perpendicular to the ring that passes through the area centroid of the ring when viewed in plan view. "Axial" or the direction of the "axis" can also be viewed as being parallel to the direction of blood flow within the valve orifice and thus within the ring when implanted therein. Stated another way, the implanted tricuspid ring orients about a central flow axis aligned along an average direction of blood flow through the tricuspid annulus. The rings of the present invention may be 3-dimensional, though portions thereof may be planar and lie perpendicular to the flow axis.

With reference to FIG. 5, an exemplary annuloplasty ring 40 of the present application is shown in longitudinal sectional view from the inflow side of the ring. The term longitudinal sectional view refers to a section through the annuloplasty ring 40 that extends around the periphery of the ring, but does not have to be in a single plane. That is, if the annuloplasty ring 40 exhibits three dimensions, in that portions bow up or down out of a nominal plane, then the longitudinal sectional view follows the contour. In other words, the sectional view of FIG. 5 is intended to encompass a variety of annuloplasty rings, planar or otherwise.

The annuloplasty ring 40 includes an inner core 42 forms of the relatively rigid material, such as stainless steel, titanium, or Cobalt Chromium (CoCr family of alloys: CoCr, L605, MP, MP25, MP35N, Elgiloy, FW-1058). The core 42 provides the "skeleton" of the annuloplasty ring 40, and is made of the material that, while it may flex to a certain degree, resists deformation from the forces experienced once implanted at the valve annulus. The ring core 42 is preferably formed from one of the relatively rigid metals or alloys listed above, or even a polymer that exhibits similar material and mechanical properties. For instance, certain blends of Polyether ether ketone (PEEK) with carbon and an alloy might be used, in which case the core could be injection molded. An exemplary construction of the ring core 42 is solid titanium or a Ti alloy such as Ti-6Al-4V (Titanium-Aluminum-Vanadium), annealed to remove residual internal stresses, extending from the first free end to the second free end.

The term "relatively rigid" refers to the ability of the core 42 to remodel a diseased heart valve annulus without substantial deformation, and implies a minimum elastic strength that enables the ring to maintain its original, or relaxed, shape after implant even though it may flex somewhat. Indeed, as will be apparent, the ring desirably possesses some flexibility around its periphery. The core 42 cannot function to remodel a valve annulus if it is entirely flexible, such as silicone or has a thin lateral profile and is made of a highly flexible metal such as Nitinol. Such flexible materials and constructions easily deform to the shape of the annulus and therefore will not maintain their original shape upon implant. In contrast, the present application presents improvements to relatively rigid "remodeling" annuloplasty rings.

The ring 40 further includes a suture-permeable interface desirably having one or more layers surrounding or covering the skeletal core 42. For instance, as with many previous annuloplasty rings, an elastomeric sleeve 44 and a fabric outer covering 46 surround the core 42. The elastomeric sleeve 44 may be silicone rubber molded around the core 42, or a similar expedient. The elastomeric sleeve 44 provides bulk to the ring for ease of handling and implant, and permits passage of sutures though not significantly adding to the anchoring function of the outer fabric covering 46. The elastomeric sleeve 44 has a constant wall thickness around a majority of the core 42 of about 0.25 mm, but may include a sewing cuff and is somewhat enlarged at the free ends as will be described. The fabric covering 46 may be any biocompatible knit or velour material such as Dacron® (polyethylene terephthalate), and desirably has a thickness of between 0.33 mm and 0.6 mm.

FIG. 5 shows a plurality of sutures 48 passing through an outer edge of the combined elastomeric sleeve 44 and outer covering 46. In a typical implant procedure, the sutures 48 are pre-installed at the annulus and brought out of the body to be threaded through the suture-permeable outer edge of the annuloplasty ring. The surgeon then pushes the annuloplasty ring down the array of sutures until it seats at the annulus. The sutures are then tied off or clipped on the accessible side of the ring.

As mentioned, the plan view shape of the annuloplasty ring 40 may be suitable for the tricuspid annulus or the mitral annulus. The illustrated annuloplasty ring 40 is particularly well-suited to be implanted at and remodel the tricuspid annulus, but if the plan view shape is modified to a generally rounded D-shape it can also function to remodel the mitral annulus.

Figure 3:
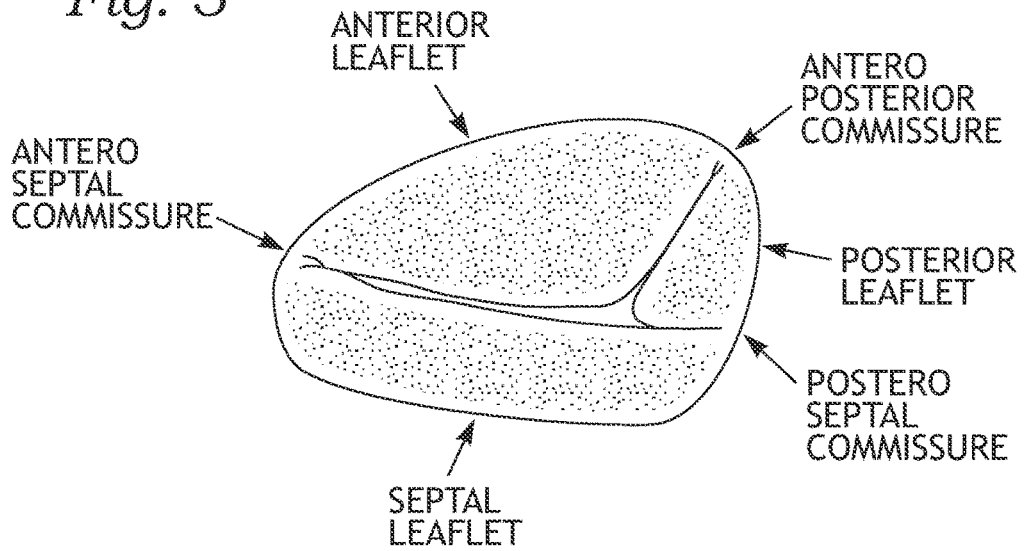
FIG. 3 is a schematic plan view of the tricuspid annulus with typical orientation directions noted as seen from the inflow side.
Figure 4:
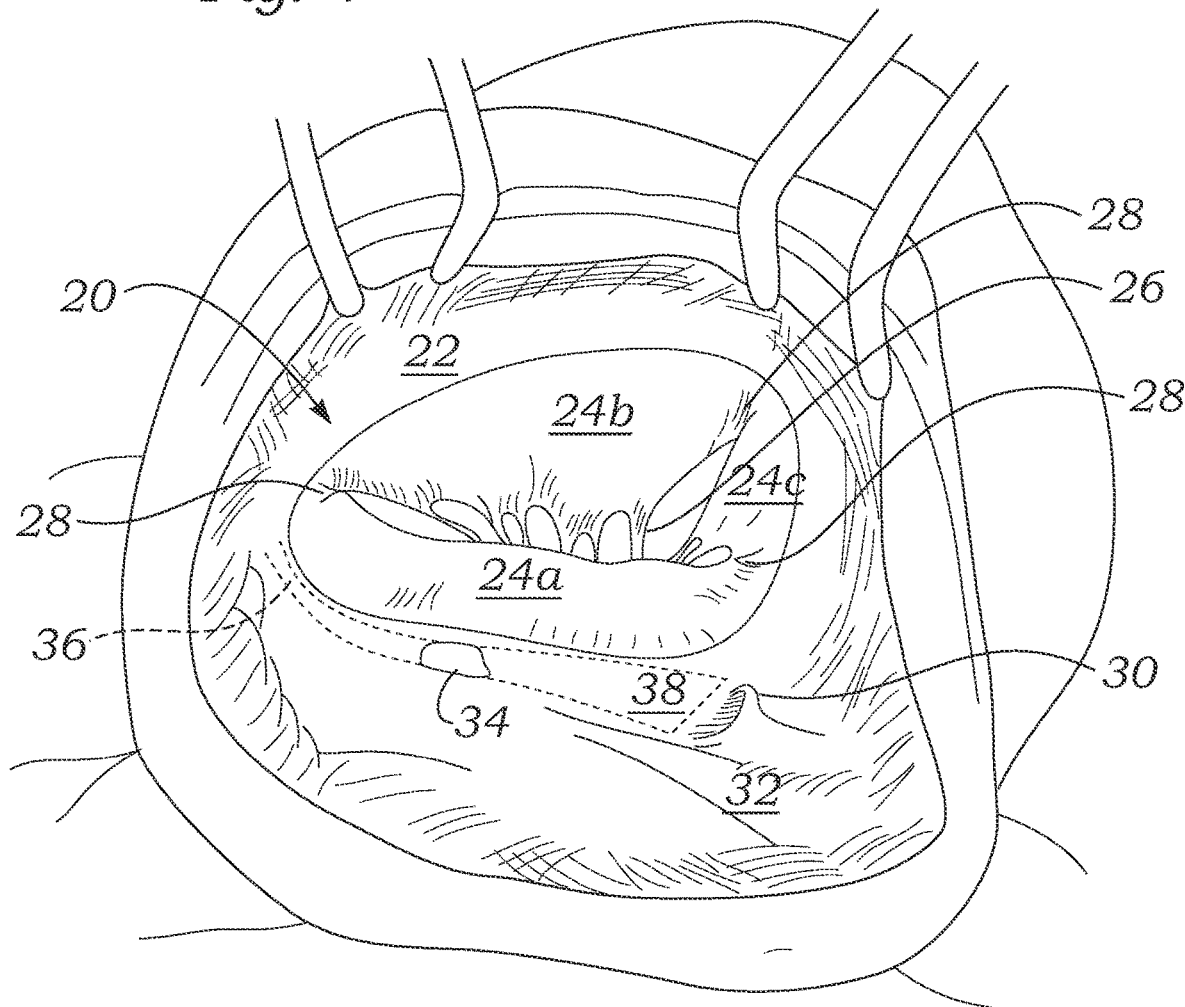
FIG. 4 is a plan view of the native tricuspid valve and surrounding anatomy from the inflow side.

As seen in FIG. 5, the illustrated embodiment shows a tricuspid ring 40, with a discontinuous or C-shaped periphery including two free ends 50, 52 that define a gap therebetween. As seen in FIG. 5, the inner core 42 preferably terminates at two free ends 54, 56 short of the free ends 50, 52 of the ring 40. The core 42 is substantially asymmetric and ovoid and when implanted the first free end 54 is located adjacent the antero-septal commissure (see FIG. 3). The ring core 42 extends from the first free end 54 in a clockwise direction, as seen looking at the inflow side in FIG. 5, around convex segments corresponding to the anterior leaflet, the antero-posterior commissure, the posterior leaflet, the postero septal commissure, and the septal leaflet within which the second free end 56 terminates. The nomenclature and shapes for these segments is taken from the standard anatomical nomenclature around the tricuspid annulus as seen in FIG. 3.

It should be further noted that the term "asymmetric" means that there are no planes of symmetry through the ring core 42 looking from the inflow side, and "ovoid" means generally shaped like an egg with a long axis and a short axis, and one long end larger than the other. As mentioned, a substantial portion of the ring core 42 may be planar, though some segments may have up or down bulges or bows.

The exemplary annuloplasty ring 40 features two enlarged regions 58 of the elastomeric sleeve 44 having the outer covering 46 thereon at the two free ends 50, 52. Preferably, the enlarged regions 58 comprise widened molded areas of the elastomeric sleeve 44 so as to be highly flexible or flaccid. Furthermore, a plurality of additional sutures 60 are installed at the free ends 50, 52 through the enlarged regions 58. These sutures 60 secure the free ends to the annulus tissue, but because of the flaccid nature of the free ends the sutures do not exert a large amount of pull-through force on the tissue or annuloplasty ring. That is, the free ends 50, 52 tend to move with the cyclic nature of the annulus movement such that the assembled components of the ring, sutures, and annulus at the free ends move together. This arrangement greatly reduces the possibility of dehiscence, especially for tricuspid annuloplasty rings.

FIGS. 5A-5C are lateral sectional views through several locations of the annuloplasty ring of FIG. 5 which illustrate a further aspect of gradually increase flexibility toward the free ends 50, 52. In one embodiment, the inner core 42 comprises a series of vertically-oriented bands 62 that are stacked together circumferentially, as seen in FIG. 5A which is taken in a midsection of the core. FIG. 5B is taken through a section near the free end 56 of the core 42, and shows how the size and even number of the bands 62 have been reduced, thus rendering the free end 56 more flexible than the mid-portion of the core 42. This gradually increasing flexibility assists in reducing stresses on the sutures 48 and 60, further lessening the chance of dehiscence.

FIGS. 5A and 5B show an outer bulge 64 formed in the elastomeric sleeve on the outer edge of the ring 40. This provides a sewing cuff facilitating passage of suture needles and reducing the chance of catching the needle on the assembly of the bands 62. FIG. 5C shows one form of the enlarged flaccid regions 58 at the free ends 50, 52. The free ends 50, 52 are shown as somewhat paddle-shaped with an axial thickness less than the remainder of the ring. However, the free ends 50, 52 may also have the same height as the rest of the ring, but just be wider as shown. Furthermore, though the free ends 50, 52 are shown with the large region 58 of the elastomeric sleeve 44, the ends may simply be an extension of the fabric cover 46 without any elastomer. In other words, the free ends 50, 52 are simply significantly more flexible than the regions of the ring 40 having the core 42.

In a preferred embodiment, the enlarged free ends 50, 52 desirably have a circumferential length as measured as an extension from the inner core 42 toward the gap in the ring 40 of between about 3-10 mm, though the ends could extend in this direction up to 20-25 mm. The radial width of the enlarged free ends 50, 52 is also desirable between about 3-10 mm.

FIG. 6 illustrates an alternative annuloplasty ring 80 that is constructed much like the ring 40 described above, and thus will have similar element numbers. Namely, the annuloplasty ring 80 includes an inner skeletal core 42 surrounded by a suture-permeable interface of the elastomeric sleeve 44 and an outer fabric cover 46. The ring 80 terminates at two free ends 50, 52, while the inner core 42 terminates at two free ends 54, 56. As with the earlier embodiments, the two free ends 50, 52 include enlarged regions 82, 84 that provide highly flexible areas through which to pass additional sutures 86. Once again, the enlarged regions 82, 84 reduce the possibility of dehiscence by moving with the cyclically moving annulus.

In contrast to the version shown in FIGS. 5-5C, the enlarged regions 82, 84 of the free ends 50, 52 of the ring 80 primarily comprise radially outward bulges from the core 42, rather than circumferential projections into the gap between the two free ends. The shape is seen in the longitudinal section view of FIG. 6, and in the radial cross-section of FIG. 6C, where the enlarged region 84 comprises a laterally outward extension of the elastomeric sleeve 44 surrounded by the fabric cover 46. Although a portion of the elastomeric sleeve 44 extends circumferentially beyond the free ends 54, 56 of the core 42 into the gap therebetween, it is nowhere near as large as the earlier embodiment.

FIGS. 6A-6C are lateral sectional views through several locations of the annuloplasty ring 80, illustrating another configuration of core 42. Namely, the core 42 comprises a generally U-shaped channel member 90 that may be made of the relatively rigid metal such as titanium. In this embodiment, the height of the channel member 90 gradually reduces around the ring from the midsection as seen in FIG. 6A until it reaches a minimum at the free ends 54, 56, as seen in FIGS. 6B and 6C. This arrangement increases the flexibility of the free ends of the core 42 primarily in bending about substantially radial axes. That is, the cross-section of the core 42 remains somewhat stiffer in bending within the plane of the ring, and more easily bends up and down.

FIGS. 6A-6C also illustrate an outwardly projecting sewing flange 92 formed by the molded elastomeric sleeve 44. Desirably, the sewing flange 92 extends around the entire periphery of the ring 80. In an exemplary embodiment, the radial extent of the enlarged region 84 is between 2-4 times as large as the radial extent of the sewing flange 92. That is, the "radial extent" of either the sewing flange 92 when enlarged region 84 is that distance projecting outward from the bulk of the elastomeric sleeve 44 surrounding the core 42. For example, the radial extent of the sewing flange 92 is given as dimension A, while the radial extent of the enlarged region 84 is given as dimension B. The ratio of B to A is between 2:1 to 4:1. In absolute terms, the sewing flange 92 may have a dimension A of 1-2 mm, while the dimension B of the enlarged region 84 is between 2-8 mm.

FIG. 7 is a longitudinal sectional view of an alternative annuloplasty ring 40' similar to the ring in FIG. 5, and thus will have similar element numbers. The ring 40' has enlarged regions 58 of the elastomeric sleeve 44 at the two free ends 50, 52 of the ring project circumferentially toward each other. However, the gap between the free ends 54, 56 of the core 42 is larger than that in FIG. 5, and is more like the gap shown in FIG. 6. Because the core free ends 54, 56 are father apart, the floppy ends 58 are also farther apart. This illustrates that the gap between the two free ends 50, 52 can be quite large, up to about half the major dimension of the entire ring.

FIGS. 7A-7C show the annuloplasty ring of FIG. 7 in various sections, much like the sections in FIGS. 5A-5C of the earlier ring. One change is that the floppy ends 58 may be longer than before, so that section 7B shows a neck portion 94 of the elastomeric sleeve 44 beyond the core free end 56 and before the enlarged region 58.

FIG. 8 illustrates a still further annuloplasty ring 96 of the present application which again exhibits floppy ends 98 beyond the free ends 54, 56 of the core 42. In this embodiment, the floppy ends 98 are not necessarily radially larger than the remainder of the ring, as shown in cross-section in FIG. 8C. The floppy ends 98 may be flattened, as shown, or more cylindrical. The free ends 54, 56 of the core 42 are significantly far apart so that the floppy ends 98 extend longer than previously shown. For instance, the floppy ends 98 may extend a distance L of between about 20-25 mm past the free ends 54, 56 of the core 42.

Figure 9:
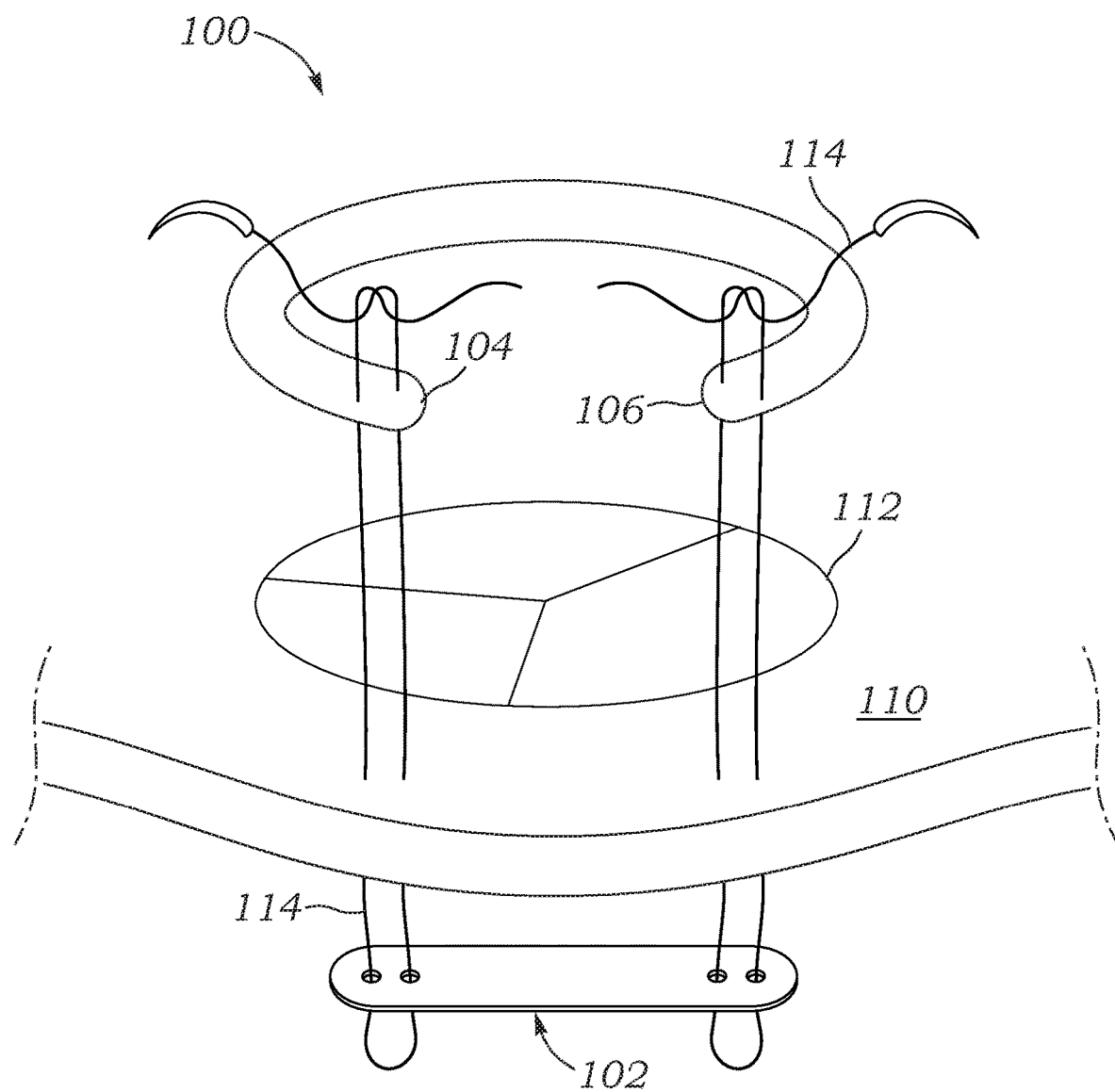
FIG. 9 is a schematic illustration of an exemplary assembly of an annuloplasty ring and a securing plate for stabilizing free ends of the annuloplasty ring.

In addition to providing enlarged floppy ends for the annuloplasty rings, as described above, the free ends may also be secured using specialized pledgets. FIG. 9 is a schematic illustration of an exemplary assembly of an annuloplasty ring 100 and a securing plate 102 for stabilizing the free ends 104, 106 exploded on either side of a valve annulus 110. A tricuspid valve 112 in the annulus 110 is remodeled by the ring 100. Sutures 114 pass through the highly flexible or floppy free ends 104, 106 of the ring 100, through the valve annulus 110, and through the securing plate 102. Each suture 114 then passes back upward through the securing plate, through the valve annulus, and again through the respective free end 104, 106, to be tied off. The presence of the securing plate 102 further helps stabilize the floppy free ends 104, 106 relative to the annulus 110 without adding rigidity to the structure. Because the securing plate 102 is made of fabric or other flexible material, the free ends 104, 106, and sutures 114 all can move with movement of the annulus. This greatly reduces the chance of pull out of the sutures from the free ends of the ring or from the heart annulus tissue.

As with existing rings, rings of the present application are available in sizes 26 mm through 36 mm in 2 mm increments, having outside diameters (OD) between 31.2-41.2 mm, and inside diameters (ID) between 24.3-34.3 mm. These diameters are taken along the "diametric" line spanning the greatest length across the ring. It should be mentioned, however, that the present invention is not limited to the aforementioned range of sizes, and rings smaller than 24 mm or larger rings of 38 or 40 mm OD are also possible, for example. The "ring size" is the size labeled on the annuloplasty ring packaging.

Several typical steps in the implant procedure will be explained. First, the surgeon utilizes valve annulus sizers to measure the tricuspid valve for annuloplasty ring size. Typical sizing technique for tricuspid valve annuloplasty includes assessment of septal leaflet length using two notches on a plate-like sizer (such as Tricuspid Sizers available from Edwards Lifesciences of Irvine, Calif.), and evaluation of anterior leaflet surface area. The surgeon should not attempt to deform or alter the ring 40, 80 to conform to a specific annular anatomy, as it could damage the ring. Instead, if the ring 40, 80 is not suitably sized for the annulus, a larger or smaller ring should be selected.

Ultimately, the surgeon determines the proper size of ring, and the assembly of tricuspid annuloplasty ring 40, 80 and a ring holder (not shown) is provided to the operating room. The tricuspid annuloplasty ring 40, 80 is supplied in a sterile package with the ring holder. The procedure for gaining access to the tricuspid annulus involves performing a sternotomy and then stopping the heart and placing the patient on bypass. The tricuspid annulus is exposed through the right atrium. Further details on the surgical steps surrounding the tricuspid repair are well known to the surgeon.

Next, the surgeon or surgeon's assistant attaches a handle to the holder. A plurality of suture needles are passed through the outside edge of the annuloplasty ring 40, and the additional sutures 60 at the free ends 50, 52 through the enlarged regions 58. If implanting the ring 80 of FIG. 9, the securing plate 102 for stabilizing the free ends 104, 106 is placed below the valve annulus 110 and at least two sutures passed down through it. The surgeon uses the needles to pre-install a plurality of implant sutures using horizontal mattress stitches around the annulus, and thread them through corresponding locations around the ring 40, 80. No sutures are placed in the atrial tissue or through the area of the Bundle of His, which may impair cardiac conduction, nor through the right coronary artery. This is a typical implant technique for both annuloplasty rings and prosthetic heart valves and is followed by sliding or "parachuting" the ring 40, 80 down the array of pre-installed sutures into contact with the annulus.

After parachuting the ring 40, 80 down the array of pre-installed sutures into contact with the tricuspid annulus, the implant sutures are tied off using knots or possibly clips (not shown) that eliminate the time-consuming knot-tying. To increase visibility for this step, the handle may first be detached from the holder. Finally, when surgeon has secured the ring 40, 80 to the annulus with the sutures, he/she severs an attachment suture connecting the ring to the holder. Specifically, the surgeon uses a sharp implement such as a scalpel to sever the attachment suture at one or more cutting guides on the holder. Although not show in detail, the attachment sutures pass in and out of the ring 40, 80 through a holder template, and tie off at each end to the template. Severing the suture in the middle at the cutting guide permits the surgeon to simply pull the holder free from the ring. The attachment suture pulls out of the ring 40, 80 at the same time.

Finally, the tricuspid annuloplasty ring 40, 80 is fully implanted at the tricuspid annulus, with the implant sutures and knots holding it in place. The annulus is reshaped such that the valve leaflets coapt and prevent regurgitation.

The surgeon and his/her team then evaluates the quality of the repair by ventricular pressurization via bulb syringe then transesophageal echocardiography (TEE) after completion of cardiopulmonary bypass. Care in the measurement of the orifice, annuloplasty ring selection, and insertion technique are essential in achieving a good result. However, associated subvalvular lesions may necessitate additional procedures. If careful application of the annuloplasty ring 40, 80 fails to produce adequate repair of valvular insufficiency as determined by echocardiography, visual inspection, or intraoperative testing, the surgeon may ultimately remove the ring 40, 80 and replace the diseased valve with a prosthetic valve during the same procedure.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. A prosthetic tricuspid annuloplasty ring, comprising:
a ring core made of a relatively rigid material and defining a discontinuous periphery around an axis along an inflow-outflow direction with a first free end separated from a second free end across a gap; and
a suture-permeable interface that surrounds the ring core along its length and extends circumferentially from both free ends into the gap to form floppy regions through which sutures may be passed to secure the annuloplasty ring to a valve annulus, the floppy regions being axially flattened, wherein the annuloplasty ring defined by the ring core and interface has an asymmetrical ovoid shape shaped for implanting at the tricuspid annulus.

2. The annuloplasty ring of claim 1, wherein the floppy regions comprise enlarged paddle-shaped generally circular extensions.

3. The annuloplasty ring of claim 1, wherein the floppy regions are not radially larger than a portion of the suture-permeable interface surrounding the ring core.

4. The annuloplasty ring of claim 1, wherein the floppy regions extend circumferentially between about 3-10 mm past the free ends.

5. The annuloplasty ring of claim 1, wherein the floppy regions extend circumferentially between about 20-25 mm past the free ends.

6. The annuloplasty ring of claim 1, wherein the suture-permeable interface comprises an elastomeric sleeve surrounding the ring core and a fabric covering around the elastomeric sleeve.

7. The annuloplasty ring of claim 6, wherein the elastomeric sleeve is molded around the ring core and defines a shape of the floppy regions surrounded by the fabric covering.

8. The annuloplasty ring of claim 6, wherein the elastomeric sleeve is molded around the ring core, and the floppy regions comprise only the fabric covering.

9. The annuloplasty ring of claim 8, wherein the floppy regions are not radially larger than a portion of the suture-permeable interface surrounding the ring core.

10. The annuloplasty ring of claim 1, wherein the ring core comprises a solid titanium alloy member.

11. The annuloplasty ring of claim 1, wherein the ring core comprises a Cobalt Chromium alloy member.

12. A prosthetic tricuspid annuloplasty ring, comprising:
a ring core made of a relatively rigid material and defining a discontinuous periphery around an axis along an inflow-outflow direction with a first free end separated from a second free end across a gap; and
a suture-permeable interface that surrounds the ring core along its length and extends circumferentially from both free ends into the gap to form floppy ends more flexible than the ring core and through which sutures may be passed to secure the annuloplasty ring to a valve annulus, wherein the suture-permeable interface comprises an elastomeric sleeve immediately surrounding the ring core and a fabric covering around the sleeve, with the elastomeric sleeve forming no part of the floppy ends, wherein the floppy ends are not radially larger than a portion of the interface surrounding the ring core, and wherein the annuloplasty ring defined by the ring core and interface has an asymmetrical ovoid shape shaped for implanting at the tricuspid annulus.

13. The annuloplasty ring of claim 12, wherein the floppy ends are axially flattened.

14. The annuloplasty ring of claim 12, wherein the floppy ends extend circumferentially between about 20-25 mm past the free ends.

15. The annuloplasty ring of claim 12, wherein the ring core has free ends that are more flexible than a mid-portion of the ring core.

16. The annuloplasty ring of claim 12, wherein the elastomeric sleeve is molded around the ring core and defines a shape of the floppy ends surrounded by the fabric covering.

17. The annuloplasty ring of claim 12, wherein the elastomeric sleeve is molded closely around the ring core, and the floppy ends comprise only the fabric covering.

18. The annuloplasty ring of claim 12, wherein the floppy ends comprise only fabric.

19. The annuloplasty ring of claim 12, wherein the ring core comprises a solid titanium alloy member.

20. The annuloplasty ring of claim 12, wherein the ring core comprises a Cobalt Chromium alloy member.

* * * * *